United States Patent [19]

Dennis, III

[11] Patent Number: 5,782,893
[45] Date of Patent: Jul. 21, 1998

[54] NEUROMUSCULAR ELECTRICAL STIMULATOR FOR DEEP VEIN THROMBOSIS TREATMENT

[75] Inventor: George J. Dennis, III, Huntington Beach, Calif.

[73] Assignee: J.D. Medical, Inc., Huntington Beach, Calif.

[21] Appl. No.: 606,970

[22] Filed: Feb. 26, 1996

[51] Int. Cl.$^6$ .................................................. A61N 1/36
[52] U.S. Cl. .................................................. 607/48; 607/2
[58] Field of Search ........................... 607/2, 48, 50, 607/64, 65, 68, 70, 72, 73, 115, 149, 152

[56] References Cited

U.S. PATENT DOCUMENTS

| | | | |
|---|---|---|---|
| 3,516,413 | 6/1970 | McDonald et al. | 607/70 |
| 4,174,706 | 11/1979 | Jankelson et al. | 607/48 |
| 4,233,965 | 11/1980 | Fairbanks | 607/70 |
| 4,640,286 | 2/1987 | Thomson | 607/70 |
| 4,706,680 | 11/1987 | Keusch et al. | 128/640 |
| 4,867,166 | 9/1989 | Axelgaard et al. | 607/48 |
| 5,069,211 | 12/1991 | Bartelt et al. | 607/63 |
| 5,358,513 | 10/1994 | Powell, III et al. | 607/48 |

*Primary Examiner*—William E. Kamm
*Assistant Examiner*—Kennedy J. Schaetzle
*Attorney, Agent, or Firm*—G. Donald Weber, Jr.

[57] ABSTRACT

A single patient use, neuromuscular electrical stimulator for the prevention of deep vein thrombosis (DVT) and embolism by electrical stimulation of muscles is attached to the muscles (typically the calf muscles) of a patient by means of self-adhering conductive electrodes for the purpose of stimulating the muscles for the prevention of DVT.

19 Claims, 2 Drawing Sheets

NEUROMUSCULAR ELECTRICAL STIMULATOR FOR DEEP VEIN THROMBOSIS TREATMENT

BACKGROUND

1. Field of the Invention

This invention is directed to a stimulator system for medical purposes, in general, and, more particularly, to a disposable stimulator system designed to inhibit or prevent deep vein thrombosis (DVT) and subsequent embolism by increasing and/or maintaining the velocity of blood circulation by means of electrical stimulation of muscles, in particular calf muscles.

2. Prior Art

A particular problem which frequently develops during and/or after surgical procedures is referred to as thrombosis. This problem is the coagulation of blood in a blood vessel to form a clot. The clot (or clots) frequently forms in the deep veins of the leg, especially in the region of the calf.

The underlying causes of deep vein thrombosis appear to be the decreased blood circulation often found in elderly and bedridden patients. The low rate of circulation in patients often leads to blood becoming "pooled" in the soleal veins of the lower limbs. The resulting clot can travel to the lungs and cause a pulmonary embolism to occur. Post-operative DVT occurs often enough to expect the affliction of multiple patients in an institution at any given time. Therefore, it is imperative that these institutions have a reliable, cost-effective means of providing treatment for DVT.

Various prophylactic measures are available in the art. For example, pharmocologic measures can be used to decrease blood coagulability. However, drugs such as heparin and dextran increase the risk of pre-operative bleeding. Moreover, pharmacological prophylactics do not provide localized therapy but, rather, affect the entire body chemistry.

Compression devices are available but these devices often have awkward construction and can be difficult to administer to patients with open wounds or casts.

Foot pumps are relatively new mechanical treatement devices. However, the cost thereof limits the use of these devices with post-operative patients in institutional (i.e. in hospital) or home therapy applications.

Research (see the references listed infra in the Prior Art Statement) has shown that electrical stimulation of the calf muscle is a cost-effective prophylactic measure in the prevention of DVT. For example, a study by B. Lindstrom et al, based on the reasearch of A. N. Nicolaides et al, (which attempted to measure the optimal electrical stimulus on the calf) concluded that "pre-operative calf muscle stimulation with groups of impulses is free from side effects, simple to use and cheap." It was also concluded that "the safety of the method allows it to be combined with drugs that interfere with the coagulation system."

Electrical stimulation of the calf muscle is an effective means of preventing venous stasis and subsequent deep vein thrombosis. Moreover, the resulting increase in femoral vein velocity is not accompanied by the side effects associated with pharmocologic measures, such as excessive per-operative bleeding. However, reliable, inexpensive devices for providing such electrical stimulation are not available on the market.

PRIOR ART STATEMENT

The articles listed herewith represent literature relating to electrical stimulation of leg muscles to inhibit deep venous thrombosis.

Lindstrom, B. et al: Prediction and prophylaxis of post-operative thromboembolism: A comparison between per-operative calf muscle stimulation with groups of impulses and dextran 40. British Journal of Surgery, 69:633, 1982.

Nicolaides, A. N. et al: Optimal electrical stimulus for prevention of deep vein thrombosis. British Medical Journal, 3:756, 1972.

Doran, FSA, Drury, M. and Sivyer, A.: A simple way to combat the venous stasis which occurs in the lower limbs during surgical operations. British Journal of Surgery, 51:486, 1964.

Doran, FSA and White, H. M.: A demonstation that the risk of post-operative deep venous thrombosis is reduced by stimulating the calf muscles electrically during the operation. British Medical Journal, 54:686, 1967.

Klecker, N. and Theis, W.: Transcutaneous electric muscle stimulation—a "new" possibility for the prevention of thrombosis? Vasa 23:23, 1994.

Martella, J., et al: Prevention of thromboembolic disease by electrical stimulation of the leg muscles. Archives of Internal Medicine, 30:711, 1949.

Tichy, V. L. and Zankel, H. T.: Prevention of venous thrombosis and embolism by electrical stimulation of calf muscles. Archives of Internal Medicine, 35:24, 1954.

SUMMARY OF THE INSTANT INVENTION

This invention is directed to a neuromuscular electrical stimulator for the prevention of deep vein thrombosis (DVT) and embolism by electrical stimulation of muscles. In particular, self-adhering conductive electrodes are provided in order to be attached to the calf muscles of a patient for the purpose of stimulating the calf muscles for the prevention of DVT. The self adhering electrodes are adapted to stay on skin for up to seven (7) days to prevent DVT.

The stimulator is small, portable, with simple to use pre-attached lead wires, pre-loaded batteries, self adhering electrodes, and pre-set electrical parameters. The stimulator is inexpensive, which will promote greater home compliance with medical protocol than previously known compression devices. Therefore, it is a cost-effective system for treating DVT and is uniquely adapted for single patient usage.

The stimulator is intended to adhere to the mandatory performance standard proposed by the FDA on Jun. 19, 1995 which requires that "any lead wire intended to provide electrical contact between a patient and any medical device" shall be "protected such that the connector at the lead wire end that is connected to the patient cannot make conductive contact with an AC electrical power source."

DESCRIPTION OF A PREFERRED EMBODIMENT

Figure 1:
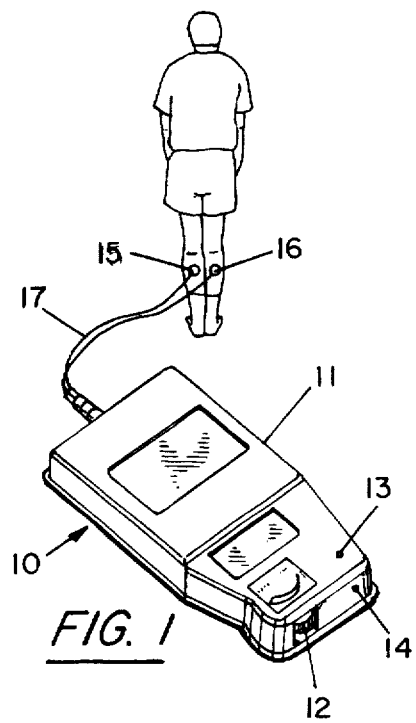
FIG. 1 is a schematic representation of the instant invention in conjunction with a patient.

Referring now to FIG. 1, there is shown a schematic representation of the system 10 of the instant invention used in conjunction with a patient.

The system 10 includes a suitable housing 11. The shape of housing 11, as shown, is representative of an actual device. However, the shape or configuration of the housing 11 can be altered as desired.

The output signals of the system are supplied to electrodes 15 and 16 which are, typically, connected to conductors which are bundled together in cable 17. The electrodes 15 and 16 are adapted to be applied or affixed to the calves of the patient for purposes of applying signals to stimulate calf muscles of the patient to prevent the venous thrombosis problem.

The housing 10 includes a thumb wheel 12 which is used to activate the circuit and, as well, control the frequency operation thereof.

A low battery light 14, typically a red light, is an optional feature but is shown in FIG. 1 for convenience. The light 14 is utilized to provide an indication that the battery included in system 10 is below a prescribed level.

The operating light 13, typically an orange light, is shown on the front of the unit to indicate the operation of the unit per se.

Very briefly, in order to utilize the system shown in FIG. 1, the electrodes 15 and 16 are applied to the calves of the patient. The thumb wheel 12 is rotated to activate a switch to turn on the electrical system in housing 10 and, then, to control the amplitude of the pulses generated thereby. The thumb wheel 12 is activated to increase the amplitude of the signal until a small muscle twitch occurs in each calf. The thumb wheel 12 is activated only when the operating light 13 is lit to indicate that the electrical system is operational. The unit is connected to the patient continuously in order to prevent the occurence of DVT. Typically, the electrical system will apply pulses to the electrodes for a prescribed period such as five seconds and then turn off for five seconds, i.e. five seconds on, five seconds off, repetitively. Of course, any other suitable treatment protocol can be utilized.

When the optional battery light 14 is activated, the battery (see infra) in the system is below a desired level and should be replaced.

Figure 2:
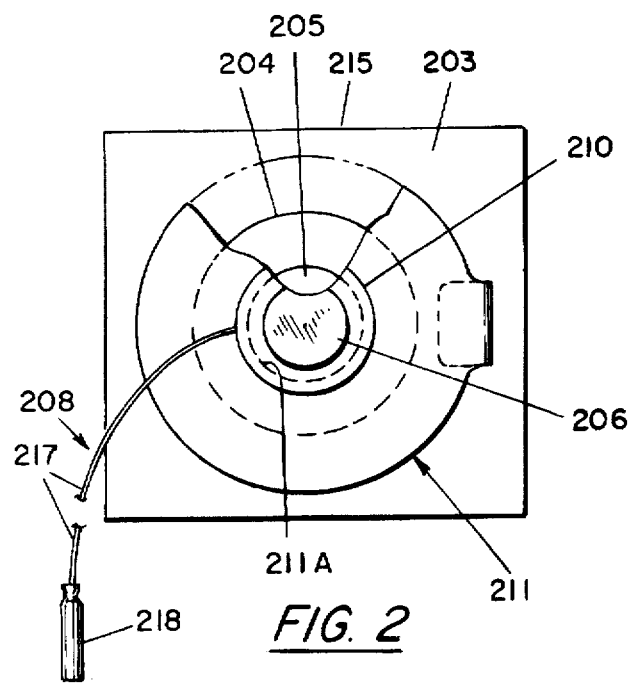
FIG. 2 is a plan view of an electrode used with the system of the instant invention.

Referring now to FIG. 2, there is shown an illustration of a plan view of a typical electrode 215 which is representative of the electrodes 15 and/or 16 shown in FIG. 1. The electrode 215 includes a suitable release paper 203 for supporting the electrode until it is applied to the patient. The release paper can be any glossy paper or the like as is known in the industry.

A relatively large foam pad 211 is utilized to adhere the electrode to the patient when the pad is removed from the release paper 203. In a typical application, the foam pad 211 is approximately three inches in diameter and includes a suitable adhesive on the inner surface thereof, i.e. the surface which is mounted on release paper 203 and, then, adhered to the patient. The foam disk 211 includes a central aperture 211A therethrough to receive the conductor wire as described infra.

A conductive gel plate 204 comprising a suitable conductive material is disposed on the inner surface of foam pad 211. Typically, the conductive gel plate 204 is approximately two inches in diameter and is adhered to the under surface of the foam disk 211. The gel plate 204 is a sticky adhesive material which adheres to the skin of the patient.

A cover 206 is placed on the outer surface of foam disk 210 to provide an indicia such as a color coded label for the electrode. This indicia permits the user to distinguish between other electrodes used in a system which includes multiple electrodes.

Foam disk 210, typically, about 1¼" in diameter, has the outer circumferential surface portion thereof adhered to the outer surface of foam pad 211. Disk 210 overlies a central aperture 211A in foam pad 211.

Foam disk 205 is disposed on the inner surface of foam disk 210 adjacent the aperture 211A in foam pad 211 and supports the conductive wires described subsequently.

A wire assembly 208 provides an elongated conductor 217 (for example as part of cable 17) which includes a connector 218 at the outer end thereof which is adapted to interconnect with the housing 11 of system 10 shown and described relative to FIG. 1. The other end of the elongated conductor 217 is joined to the electrode 211 by an electrically conductive polyester cover 209, as described hereinafter.

A tab 212 is provided at the outer edge or periphery of the foam pad 211. The tab 212 is adapted to assist in the application and/or removal of the electrode from the patient's leg or other body part. In one embodiment, the tab 212 is folded under itself to prevent the tab from adhering to the skin of the patient.

Figure 3:
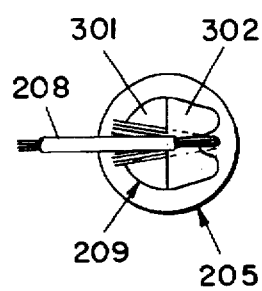
FIG. 3 is an enlarged, detailed portion of the electrode shown in FIG. 2.

Referring now to FIG. 3, there is shown an enlarged, detailed drawing of the connection of the conductor 208 of the wire assembly 218 to the electrode.

The wire 208 is shown as a braided wire. The wire is stripped at the end thereof and the several individual strands are folded back on each other. In addition, the wire strands are spread out to ensure good contact with the conductive metallic foil cover 209.

The wire 208 is affixed to conductive cover 301 which is in the form of a semicircular metal foil pad. The wire and conductive cover 301 are placed on the horseshoe shaped metallic foil 302 on the inner surface of foam disk 205. This combination is then adhered to the inner surface of the conductive gel plate 204 wherein a conductive connection to the patient's body is achieved.

Figure 4:
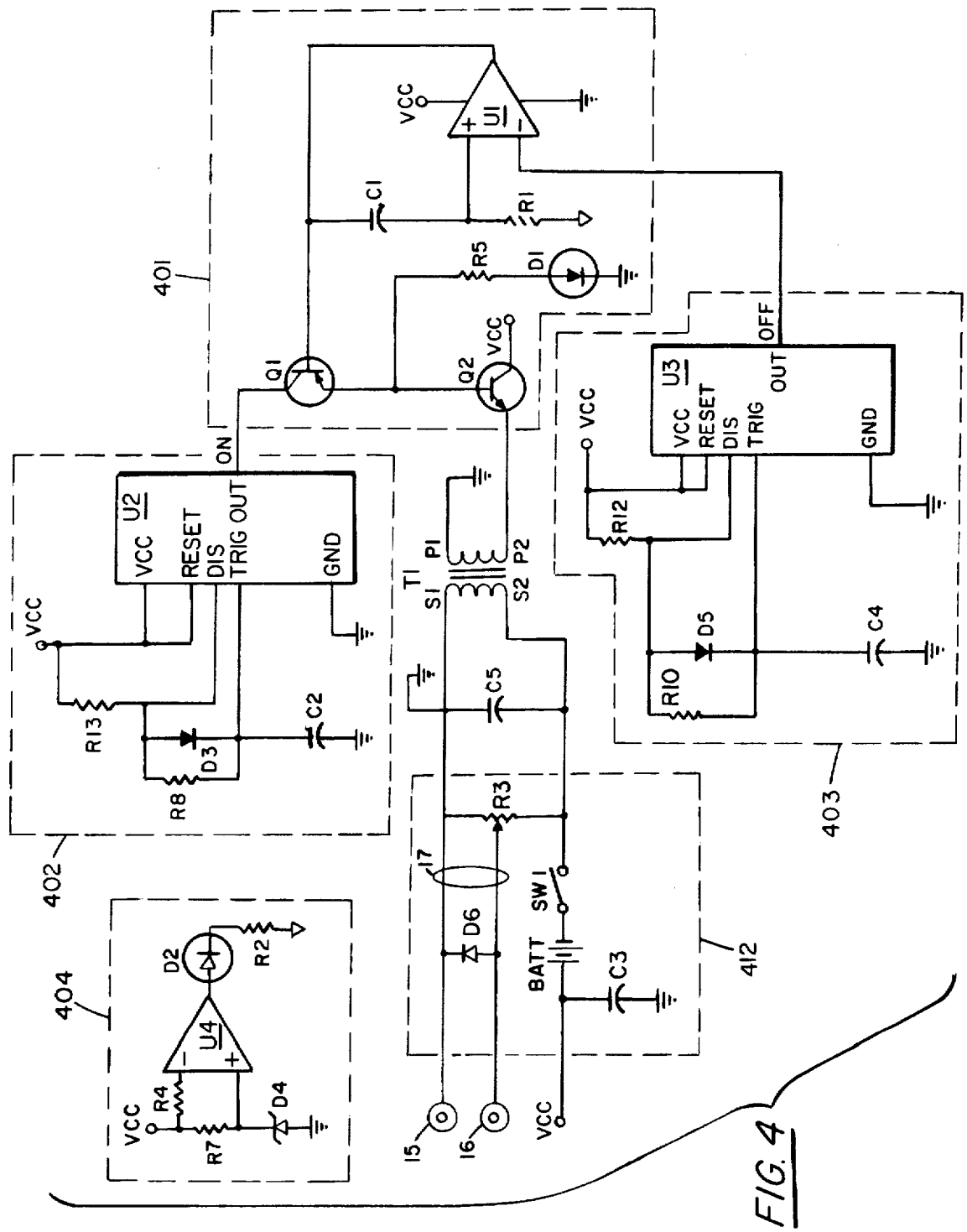
FIG. 4 is a schematic diagram for the system of the instant invention.

Referring now to FIG. 4, there is shown a schematic circuit diagram of the electrical system of the instant invention. This circuit is contained within housing 11 shown in FIG. 1. In FIG. 4, the electrodes 15 and 16 are shown schematically. The conductors of electrodes 15 and 16 are bundled together as part of cable 17.

Variable resistor R3 is part of switch SW1 (shown in dashed outline 412 which is representative of thumb wheel 12 in FIG. 1). That is, switch SW1 is connected in series with potentiometer R3 and attached thereto so that operation of the wiper arm of potentiometer R3 (by rotating thumb wheel 12) activates switch SW1 at one end of the travel thereof.

As seen, the conductor connected to electrode 15 is connected to one end of potentiometer R3 which is also connected to ground. The conductor connected to electrode 16 is connected to the wiper arm of potentiometer R3.

Diode D6 is connected across the electrode conductors to prevent negative signal spikes on the output signals produced at the electrodes.

The other end of potentiometer R3 is connected via switch SW1 to the battery BATT. The positive side of the battery produces the output voltage VCC. When switch SW1 is closed, it completes the circuit between the battery and the potentiometer. By adjusting the potentiometer R3 (i.e. adjusting thumb wheel 12 in FIG. 1) the output voltage is adjusted between electrodes 15 and 16. A filter capacitor C3 is connected to the VCC output terminal to remove any spurious noise or the like from the power supply signal.

The secondary winding of coupling transformer T1 is connected across potentiometer R3. Filter capacitor C5 is connected in parallel with the secondary winding and the potentiometer R3.

The primary winding of transformer T1 is connected between ground and the source electrode of NPN transistor Q2. The drain electrode of the transistor Q2 is connected to the source VCC.

The gate electrode of transistor Q2 is connected to the source electrode of PNP transistor Q1. The drain electrode of transistor Q1 is connected to the output of timer U2. The gate electrode of transistor Q1 is connected to the output of operational amplifier (or op-amp) U1. The output of op-amp U1 is also connected to the input of op-amp U1 via the feedback path comprising capacitor C1 and the series connected pull down resistor R1 which is connected to ground. The other input of op-amp U1 is connected to the output terminal of timer U3.

Diode D1, a light emitting diode (LED), connected in series with resistor R5 between the source electrode of transistor Q1 and ground, is equivalent to the operating light 13 shown in FIG. 1.

The circuit enclosed in outline 401, including op-amp U1, transistors Q1 and Q2 and the related components comprises a circuit which produces signals that are turned on and off by two timers and an op-amp (see infra). Diode D2 operates as an operational indicator to indicate that the device is operating and producing output pulses at electrodes 15 and 16.

The circuitry included within dashed outline 402 is operative to control the "ON" time of the system. Circuit 402 is used to control the operation frequency (pulse duration) of the system. In circuit 402, a voltage divider network (including resistor R13, R8 and capacitor C2 connected in series) provides the disable (DIS) and the trigger (TRIG) signals to timer U2. Diode D3 is connected in parallel with resistor R8 to control the threshold level of timer U2. The timer U3 produces output signals at the output thereof. These signals are identified as ON signals.

The circuitry included within dashed outline 403 is used to control the "OFF" time of the system. Circuit 403 is similar to circuit 402 and includes timer U3 which receives the power supply signal VCC and ground to cause circuits to be powered up. A similar voltage divider circuit comprising resistors R12, R10 and capacitor C4 in series are connected to produce the disable (DIS) and the trigger (TRIG) signals to timer U3. The diode D5 is connected across resistor R10 to control the threshold level of timer U3. The timer U3, similar to timer U2, produces output signals at the output thereof. These signals are identified as OFF signals.

The output of timer U2 is connected to the drain electrode of transistor Q1 in the signal (or pulse) producing circuit 401 and selectively turns transistor Q1 "ON". Thus, the output signals produced by the timer U1 are passed through transistor Q1 and applied to the base electrode of transistor Q2 to selectively turn transistor Q2 "ON" and "OFF" in order to produce a pulse pattern across primary winding of tranformer T1. This pulse pattern is then induced into the secondary winding of the transformer T1 and applied to the electrodes 15 and 16. The amplitude (or voltage level) of the pulse applied to the electrodes is determined by the setting of resistor R3 which is, in effect, a voltage divider.

The output signals of timer U3 are supplied to one input of operational amplifier U1 which, effectively, causes the amplifier to be turned OFF. In this condition, no signals are provided to the gate electrode of transistor Q1. Thus, no signals are supplied to transistor Q2 or across the transformer T1 whereupon the output electrodes 15 and 16 receive no signals. The timing of the respective signals from timer U2 and U3 is discussed infra.

The circuit shown in dashed outline 404 is a battery level testing circuit which can be omitted if desired. That is, resistor R7 and Zener diode D4 are connected in series between the power source voltage VCC (supplied by battery BATT) and ground. The signal VCC is supplied via resistor R4 to one input of op-amp U4. The signal produced across the voltage divider network comprising resistor R7 and diode D4 is supplied to the other input of op-amp U4. The output of op-amp U4 is connected to the anode of LED D2. The cathode of LED D2 is connected to ground via bias resistor R2.

In essence, when VCC is above a predetermined voltage level, determined by Zener diode D4, the output of op-amp U4 is turned OFF and LED D2 remains OFF. Conversely, when VCC falls below a prescribed level, the signal supplied to one input of op-amp U4 is operative to turn on op-amp U4 to produce a voltage level which activates LED D2 (see light 14 of FIG. 1, as well). When LED D2 is activated, the user of the system is advised that the battery BATT which provides the power voltage VCC is low and needs to be replaced.

Figure 5:
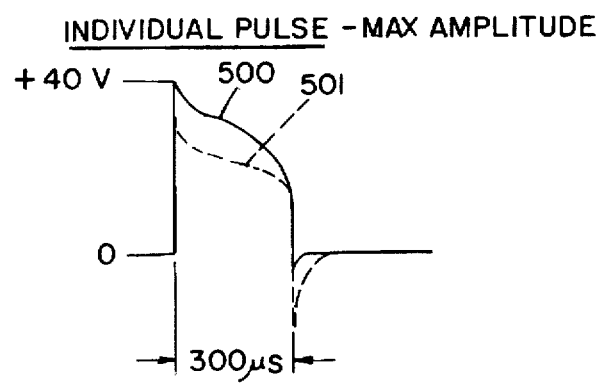
FIG. 5 is a representation of individual pulses generated by the system of the instant invention.

Referring now to FIG. 5, there is shown a schematic representation of signals generated by the circuit and applied to the electrodes 15 and 16.

The solid line signal 500 is the maximum amplitude signal which, in this case, is on the order of 40 volts. The pulse 501, indicated by the dashed outline, represents an individual pulse which has approximately 75% of the amplitude of the maximum amplitude pulse. The amplitude of the pulse 501 depends upon the setting of potentiometer R3 described above. Each of these pulses is defined to have a pulse width of approximately 300 microseconds.

In the preferred embodiment of this invention, resistors R8 and R10 are fixed resistors so that the frequency of the pulses produced by timers U2 and U3 and the pulse width thereof is fixed. It is, of course, contemplated that variable resistors can be utilized so that variations in the parameters of the pulses can be changed. However, in order to assure that the system operates at a prescribed protocol, the resistors are fixed in the preferred embodiment. In addition, this structure permits the device to be manufactured less expensively. With the lower expenses and the fixed or limited variability, the system becomes disposable which has advantages in many medical protocol situations. In addition, the fixed parameter design simplifies user instructions.

As shown in FIG. 5, the individual pulses tend to have a negative overshoot at the trailing edge thereof. However, the diode D6 tends to limit this overshoot to a very small negative pulse as shown in solid outline.

The frequency rate of the signal shown in FIG. 5 has a varying rate of five pulses per second. That is, with five pulses per second, the muscle is stimulated to contract to produce the DVT stimulation that is desired. However, this pulse rate does not mask pain in the muscles or the like. Moreover, this frequency rate is adequate to provide an appropriate number of positive ions which are concentrated at the site where the electrode is attached in order to increase blood circulation and, thus, avoid DVT thrombosis. Of course, the frequency can be made variable if so desired.

Figure 6:
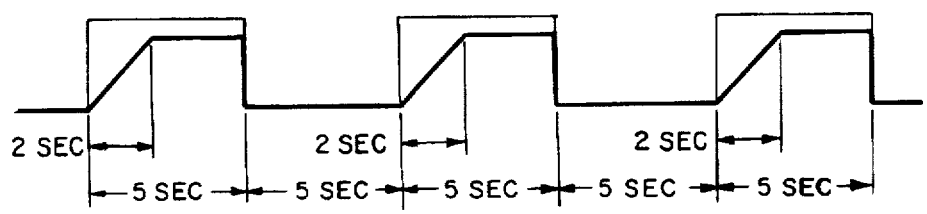
FIG. 6 is a schematic representation of a pulse train produced by the instant invention.

Referring now to FIG. 6, there is shown a schematic representation of a pulse train produced by the preferred embodiment. That is, the pulse train comprises a five-second ON period, followed by a five-second OFF period, followed by a five-second ON period and so forth.

As shown in FIG. 6, for approximately two seconds of the five second ON interval, the pulses (which are 300 microseconds in width) are ramping up to the full amplitude value controlled by the output level of op-amp U1. As is seen, the ramp up portion of the signal is substantially linear until the maximum amplitude output signal is generated. Thereafter, the maximum amplitude signals (see FIG. 5) continue to be generated until the five-second ON interval is concluded. At that time, the five-second OFF interval occurs and no signals are passed through the circuit and applied to the electrode.

After the five-second OFF interval, the five-second ON interval is repeated as noted above. These signals are, as noted above, appropriate for causing muscle facilitation to avoid DVT without masking of pain or causing unnecessary fatigue.

Thus, there is shown and described a unique design and concept of DVT stimulator system. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A signal generator comprising, first and second timer means for supplying first and second timing signals, respectively, each of said first and second timer means includes an operational amplifier and an input control circuit, each said input control circuit establishes a constant input voltage to the respective operational amplifier whereby the respective timing signals produced by each of said timer means have a constant frequency, pulse producing means including a further operational amplifier connected to said second timer means to receive said second timing signal and to produce pulses representative of said second timing signals, electronic switching means connected to said further operational amplifier and controlled by the pulses produced thereby, control means connected to said pulse producing means to receive said pulses therefrom and to control the amplitude thereof, said electronic switching means connected to selectively supply said first timing signal to said control means, and output means connected to said control means to receive said pulses therefrom.

2. The signal generator recited in claim 1 including, electrical coupling means connected between said pulse producing means and said control means.

3. The signal generator recited in claim 2 wherein, said electrical coupling means comprises inductively coupled coil means.

4. The signal generator recited in claim 1 wherein, said control means includes variable impedance means for controlling the amplitude of said pulses.

5. The signal generator recited in claim 4 wherein, said variable impedance means comprises potentiometer means.

6. The signal generator recited in claim 1 wherein, each said input control circuit includes an RC circuit connected to inputs of said operational amplifier to produce Trigger and Disable signals which control the operational amplifier and the frequency of the respective timing signals produced thereby.

7. The signal generator recited in claim 1 wherein, said electronic switching means includes first transistor means connected to the output of said further operational amplifier and selectively activated thereby, and second transistor means connected between said first transistor means and said control means.

8. The signal generator recited in claim 7 wherein, said first transistor means selectively passes said first timing signals from said first timer means through said second transistor means to said control means.

9. The signal generator recited in claim 7 including, light emitting means connected to said first transistor means for indicating when said first transistor means is activated.

10. The signal generator recited in claim 1 including, power source means.

11. The signal generator recited in claim 10 wherein, said power source means comprises battery means.

12. The signal generator recited in claim 11 including, battery output voltage level sensing means connected to said battery means and capable of detecting the voltage level of said battery means.

13. The signal generator recited in claim 12 including, light emitting means connected to said battery output voltage level for indicating the detection of a predetermined voltage level of said battery means.

14. The signal generator recited in claim 10 including, switch means connected between said power source means and said control means to selectively activate the signal generator.

15. A battery operated electrical muscle stimulator comprising, the signal generator recited in claim 1, said output means includes a pair of electrodes for selective attachment to a human patient, battery means for supplying power to said signal generator, battery output voltage level sensing means connected to said battery means and capable of detecting the voltage level of said battery means, and light emitting means for indicating the detection of a predetermined voltage level of said battery means.

16. The signal generator recited in claim 15 wherein, each of said electrodes includes a pad with an adhesive on one surface thereof, and an electrical conductor secured at said one surface.

17. The stimulator recited in claim 15 wherein each of said electrodes includes, a foam pad, an electrically conductive gel plate on a surface of said foam pad, and an elongated conductor connected to said conductive gel plate.

18. The stimulator recited in claim 15 including, indicator means connected to said controller means and operative to indicate when said controller means is turned on.

19. The stimulator recited in claim 15 including, housing means for enclosing said signal generator.

* * * * *